United States Patent [19]

Contractor et al.

[11] Patent Number: 5,519,149
[45] Date of Patent: May 21, 1996

[54] VAPOR PHASE CATALYTIC OXIDATION OF N-BUTANE TO MALEIC ANHYDRIDE INCORPORATING IN SITU CATALYST CALCINATION/ACTIVATION

[75] Inventors: Rashmikant M. Contractor; Harold S. Horowitz, both of Wilmington; Gregg M. Sisler, Newark, all of Del.

[73] Assignee: E. I. Du Pont de Nemours and Company, Wilmington, Del.

[21] Appl. No.: 330,770

[22] Filed: Oct. 28, 1994

[51] Int. Cl.$^6$ .................................................. C07D 307/34
[52] U.S. Cl. ............................................................. 549/259
[58] Field of Search ................................................ 549/259

[56] References Cited

U.S. PATENT DOCUMENTS

| | | | |
|---|---|---|---|
| 4,371,702 | 2/1983 | Bither, Jr. | 549/260 |
| 4,518,523 | 5/1985 | Blum et al. | 502/209 |
| 4,668,802 | 5/1987 | Contractor | 549/259 |
| 4,677,084 | 6/1987 | Bergna | 502/8 |
| 5,021,588 | 6/1991 | Contractor | 549/259 |
| 5,137,860 | 8/1992 | Ebner et al. | 502/209 |

Primary Examiner—Mukund J. Shah
Assistant Examiner—King L. Wong
Attorney, Agent, or Firm—Robert B. Stevenson

[57] ABSTRACT

An improved process for selective vapor phase oxidation of n-butane to maleic anhydride involving the use of a recirculating solids reactor having a reaction zone and a catalyst regeneration zone wherein n-butane is converted to maleic acid in the reaction zone by use of a vanadium/phosphorous oxide (V/P/O) catalyst in oxidized form and the reduced vanadium/phosphorous oxide catalyst is regenerated by contact with oxygen in the regeneration zone. Replenishment of the inherent catalyst losses associated with the catalyst recycling process is accomplished by adding to the catalyst in the regeneration zone vanadium/phosphorous oxide catalyst precursor at a rate of addition that effectuates in situ calcination and activation of the vanadium/phosphorous oxide catalyst precursor while simultaneously maintaining the desired operating temperature of the n-butane to maleic anhydride conversion reaction. Such a process is useful in maintaining the high operating capacity of the reactor over an extended period of time.

5 Claims, 1 Drawing Sheet

VAPOR PHASE CATALYTIC OXIDATION OF N-BUTANE TO MALEIC ANHYDRIDE INCORPORATING IN SITU CATALYST CALCINATION/ACTIVATION

BACKGROUND OF THE INVENTION

1. Field of the Invention

This invention relates to an improved process for the selective vapor phase oxidation of n-butane to maleic anhydride over a catalyst comprising mixed oxides of vanadium and phosphorus, (V/P/O). More specifically, the invention relates to a process involving in situ calcination and activation of the V/P/O catalyst precursor.

2. Description of the Related Art

The vapor phase oxidation of n-butane to maleic anhydride over a V/P/O catalyst is a well established commercial process. A review of the prior art describing this process is given in U.S. Pat. No. 4,668,802. In improved processes described in U.S. Pat. No. 4,668,802 and U.S. Pat. No. 5,021,588 the reaction is conducted in a recirculating solids reactor having two fluidized reaction zones. The conversion of n-butane to maleic anhydride takes place primarily in one reaction zone and the catalyst, essentially stripped of gaseous species, is transported to the other reaction zone where it is re-oxidized; i.e., regenerated prior to being returned to the reaction zone.

The mixed oxide V/P/O compositions used as catalysts in these processes are known to the art. A review of the art describing V/P/O compositions and their preparation is given in U.S. Pat No. 4,371,702. The catalyst precursor composition is usually made by a process wherein a conventional vanadium compound in which the vanadium is in the +5 oxidation state, such as in $V_2O_5$ or $NH_4VO_3$, is partially reduced to the +4 oxidation state by reaction in either an aqueous or organic liquid medium. The catalyst precursor is then formed by the addition of any appropriate phosphorus compound, for example $H_3PO_4$, refluxing to bring about reaction and recovering the catalyst precursor, usually as a hydrated vanadium phosphate, by filtration and drying or spray drying. The prior art describes the desirable range of atomic ratios of phosphorus to vanadium and also the incorporation of catalyst promoters. It is desirable that the V/P/O catalyst has good attrition resistance particularly when it is used in a fluidized bed or recirculating bed reactor. The prior art relevant to attrition resistant catalyst and its preparation is reviewed in U.S. Pat. No. 4,677,084. The production of V/P/O catalysts useful for the preparation of maleic anhydride from n-butane requires controlled calcination and activation of the catalyst precursor. This is accomplished by heating the precursor under appropriate temperature, time and atmosphere conditions to accomplish dehydration, while maintaining the average vanadium oxidation state (Vox) between specified limits. For example in U.S. Pat. No. 3,915,892 each mole of hydrated vanadium phosphate, expressed as $(VO)_2H_4P_2O_9$, evolves one mole of water at 370° to 394° C., while maintaining the Vox in the range of 4.1 to 4.5. The balance of the water, an additional mole of water per mole of precursor, is removed by heating at 395° to 600° C. in a carrier gas consisting of air or an inert gas together with controlled amounts of oxygen and hydrocarbon to provide an effluent stream containing at least one volume percent of oxygen or one volume percent each of oxygen and hydrocarbon, again while maintaining the Vox in the range of 4.1 to 4.5.

SUMMARY OF THE INVENTION

It has now been discovered that the continuous operation of a recirculating solids reactor subjects the catalyst to highly abrasive conditions and even the most attrition resistant catalyst is gradually reduced to very fine material which is lost from the reactor. Thus, the catalyst inventory diminishes and needs to be replenished to maintain maleic anhydride productivity. An object of this invention is to provide a method of accomplishing this on a continuous basis, thus maintaining a very high operating capacity for the reactor over an extended period of time. In a further aspect this invention provides a means of increasing the catalyst inventory in an operating recirculating solids reactor and thereby enhancing its productivity.

In view of the above the present invention provides an improved process for the selective vapor phase oxidation of n-butane to maleic anhydride over an attrition resistant V/P/O catalyst. The improvement consists of maintaining optimum productivity or increasing productivity in a recirculating solids reactor by the intentional addition of catalyst precursor to the fluidized bed in the regenerator vessel or in the alternative the intentional addition of calcined or partially calcined catalyst precursor to the recirculating solids stream whereby catalyst precursor (optionally calcined) is converted in situ to attrition resistant, calcined/activated catalyst. The catalyst and precursor are subjected to alternating environments of catalyst reduction, in a hydrocarbon containing atmosphere and catalyst regeneration in an oxygen containing atmosphere, in successive reaction zones within a recirculating solids reactor.

V/P/O catalyst having very good attrition resistance can be initially prepared, for example by the procedures of U.S. Pat. No. 4,677,084 and by the procedure described in a commonly assigned U.S. patent application Ser. No. (case CH-2309) filed concurrently herewith and incorporated herein by reference. However when used continuously in a recirculating solids reactor, the catalyst inventory gradually decreases due to comminution and subsequent loss as fine dust. Thus, the catalyst must be replenished to maintain maleic anhydride productivity. It has been discovered that catalyst precursor, prepared for example by these procedures when added to the fluidized bed in the regenerator vessel undergoes calcination/activation and is converted in situ to effective catalyst. The unique and unexpected features of the invention are:

(a) attrition resistance sufficient to maintain prolonged catalyst life during subsequent recycling through a recirculating bed solids reactor can be imparted in the regenerator vessel in a short period of time, usually less than 5 minutes;

(b) calcination and activation are accomplished in a cyclic environment within a reasonably short time despite the fact that the temperature is about 100° C. lower than is normally used for catalyst activation.

Thus the process of this invention provides a means of generating active V/P/O catalyst in situ in a recirculating bed solids reactor, producing maleic anhydride by oxidizing n-butane, while maintaining its efficient operation.

DESCRIPTION OF THE PREFERRED EMBODIMENTS

Figure 1:
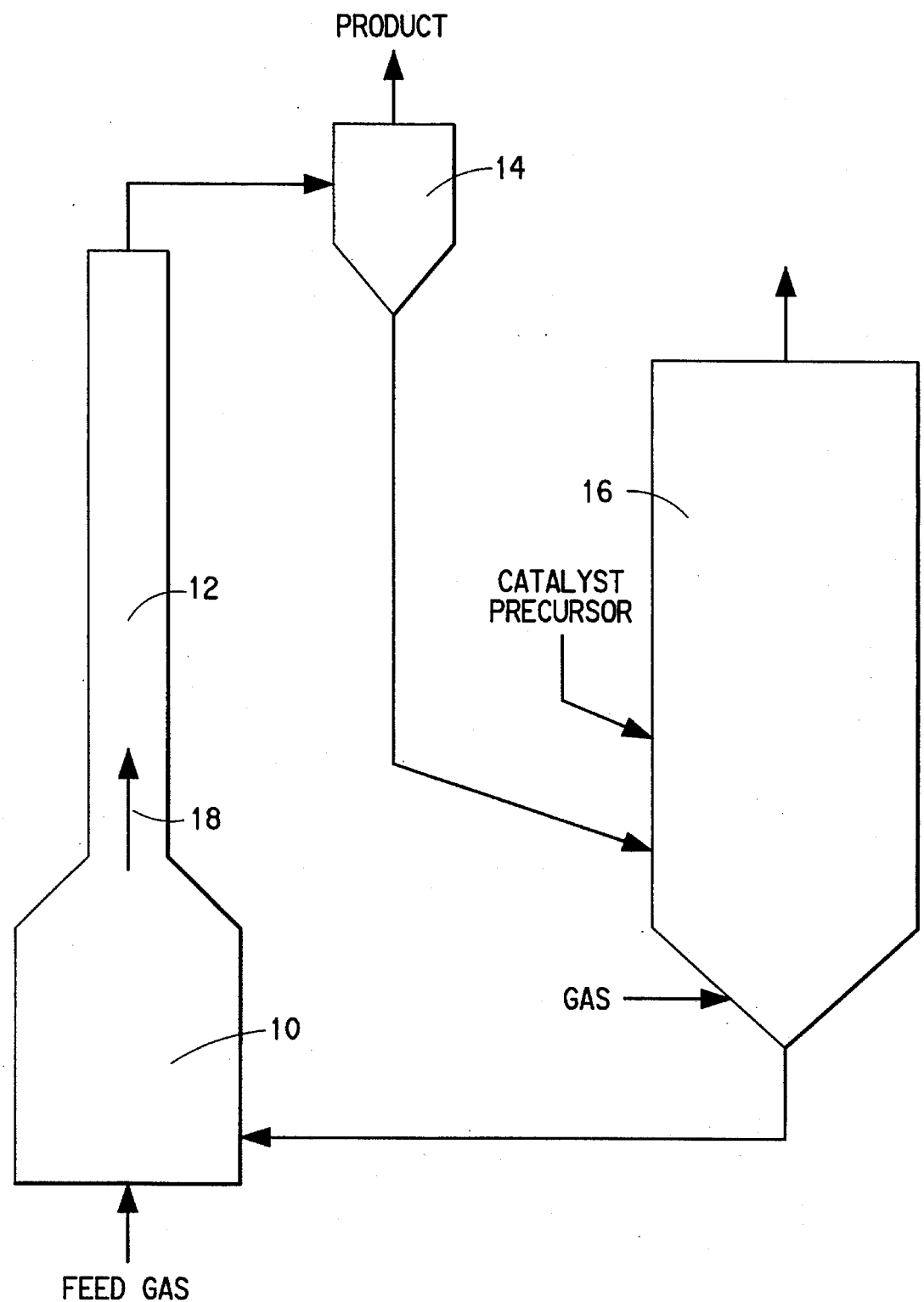
FIG. 1 shows a schematic drawing of a recirculating solids reactor configuration in which the reaction zone is comprised of two parts, a fluid bed section and a riser section, and the regeneration zone is comprised of a fluid bed section.

This invention relates to an improved process for the selective vapor phase oxidation of n-butane to maleic anhydride over an attrition resistant catalyst containing mixed oxides of vanadium and phosphorus. The improvement involves maintaining or increasing productivity in a recirculating solids reactor by generating fresh catalyst by the addition of catalyst precursor to the fluidized bed in the catalyst regenerator vessel or by addition of calcined or partially calcined catalyst precursor to the recirculating solids stream whereby this added catalyst precursor is converted in situ to attrition resistant, calcined/activated catalyst. The catalyst and precursor are subjected to alternating environments of catalyst reduction, in a hydrocarbon containing atmosphere and catalyst regeneration in an oxygen containing atmosphere in successive reaction zones within a recirculating solids reactor.

The improved process for the selective vapor phase oxidation of n-butane to maleic anhydride includes;

(a) providing a recirculating solids reactor comprising a reaction zone and a catalyst regeneration zone;

(b) contacting in a reaction zone a feed gas containing about 1 mole % to 100 mol %, preferably about 5 mole % to about 20 mole %, n-butane, 0 to 20 mol % oxygen, and the remainder, to 100 mole %, inert gas, with an effective amount of attrition resistant V/P/O catalyst, in oxidized form, comprised of particles about 20 to about 300 μm in size, in the reaction zone of a recirculating solids reactor, at a temperature of about 360° C. to about 500° C., preferably 360° C. to 450° C. at a gas residence time in the reaction zone of about 0.5 second to about 15 seconds, a catalyst residence time in the reaction zone of about 2 seconds to about 5 minutes, and a gas exit pressure of 0 psig to 50 psig;

(c) removing the effluent produced in step (b) from the reaction zone and separating the resultant reduced catalyst from the effluent gases, preferably stripping off any effluent gases from the reduced catalyst, transporting the reduced catalyst to the regeneration zone of the recirculating solids reactor, and recovering maleic anhydride from the effluent gases;

(d) adding to the catalyst in the regeneration zone or to the catalyst being recirculated sufficient V/P/O catalyst precursor or calcined precursor, respectively, which precursor is attrition resistant or designed to be attrition resistant after calcination, to at least replenish catalyst losses in the recycling process; an amount of catalyst precursor in the range of 0.10 wt % to 15 wt % can be added at any one time, the only restriction being that the rate of addition not be so great that the recirculating bed reactor temperature be decreased substantially below the desired operating temperature range;

(e) oxidizing the reduced catalyst and calcining the added catalyst precursor in the regeneration zone using gas containing about 4 mole % to 25 mole %, preferably about 21 mole % oxygen, with the remainder up to 100 mole %, being inert gas at a temperature of about 360° C. to about 500° C., preferably 360° C. to 450° C. at a catalyst residence time in the regeneration zone of up to 5 minutes, at an oxygen-containing gas residence time of up to about 30 seconds and a gas exit pressure of 0 psig to 50 psig; and (f) recycling the oxidized and freshly calcined catalyst from step (e) to the reaction zone and continually repeating steps (b), (c), (d) and optionally (e) so that the added precursor gradually undergoes calcination and activation.

The improved process employs a recirculating solids reactor. Recirculating solids reactors can have many different reactor/regenerator configurations. For example, the reaction zone of the reactor can be comprised of a riser reactor, a fluidized bed reactor, a moving bed reactor, or a combination of both a fluidized bed reactor and a riser reactor. Similarly, the regeneration zone of the regenerator can be comprised of a riser reactor, a fluidized bed reactor, or a combination of both a riser reactor and a fluidized bed reactor. It is to be understood that the invention is not limited to the specific combinations of reactors recited above. A riser or transport line reactor is characterized by high gas velocities of from about 5 ft/s (about 1.5 m/s) to greater than 40 ft/s (12 m/s). Typically, the reactor line is vertically mounted with gas and solids flowing upward in essentially plug flow. The flow can also be downward and the reactor line can be mounted other than vertically. With upward flow of gas and solids, there can be a significant amount of local back mixing of solids, especially at the lower end of the velocity range. The solids concentration in the reaction zone of the reactor can range from, typically, about 1 lb/ft$^3$ (16 kg/m$^3$) to, typically, about 10 lb/ft$^3$ (160 kg/m$^3$), depending on the gas velocity, catalyst particle size and density, and the catalyst circulation rate. A fluidized bed reactor is characterized by extensive solids back mixing. The gas velocity ranges from about a few inches per second (5–10 cm/s) to about 3 ft/s (about 1 m/s) and the solids concentration ranges from about 20 lb/ft$^3$ to about 45 lb/ft$^3$ (about 300 kg/m$^3$ to about 700 kg/m$^3$) for the V/P/O catalyst used in the process of this invention having the catalyst a bulk density of about 50 lb/ft$^3$ (about 800 kg/m$^3$). The lower gas velocity and the larger fluidized bed volume makes the fluidized bed a preferred location to install heat exchangers to remove heat and control temperature.

The oxidation of n-butane by the V/P/O catalyst in oxidized form and the oxidation of reduced catalyst by gas phase oxygen along with calcination of the freshly added catalyst in precursor form are carried out in separate zones of the reactor, with the conditions for each zone chosen to optimize the step being carried out in that zone without any restrictions imposed by the demands of the other step. Activation of the freshly added catalyst in precursor form is carried out continuously as the catalyst circulates between the reaction and regeneration zones. Some reoxidation of the catalyst may be carried out in the reaction zone in addition to that carried out in the regeneration zone, if desired, by introducing some gas phase oxygen into the reaction zone.

The preferred selection of the reactor and regenerator configurations depends on the activity of the catalyst, the attrition resistance of the catalyst, the relative rate of catalytic degradation of maleic anhydride compared to the production of maleic anhydride, the amount of gas phase oxygen used in the reactor zone, the need for a large fluidized bed volume to accommodate heat exchangers, and the impact of these elements on the overall economics.

FIG. 1 is a schematic drawing of a recirculating solids reactor in which the process of the invention can be conducted. The reaction zone is composed of a fluidized bed section 10 and a riser section 12. The feed gas enters 10 and the oxidation of n-butane takes place in sections 10 and 12. The separator-stripper unit 14 separates and strips off the reaction zone effluent gases from the reduced catalyst. The maleic anhydride product is recovered from the reactor effluent gases leaving 14. The reduced catalyst is transported to the regeneration zone which is comprised of the fluidized bed section 16. As shown in the figure, attrition resistant V/P/O catalyst precursor or V/P/O precursor, designed to become attrition resistant subsequent to calcination, is introduced into the fluidized bed of the regeneration zone 16 in an amount at least sufficient to replenish catalyst losses which occur during the continuous recycling process. Optionally, the catalyst precursor or V/P/O precursor can be calcined or partially calcined in a separate water removal vessel (not shown) and then introduced into the recirculating solids stream of either the reactor or regenerator. According to the present invention it may at times be desirable to increase the catalyst inventory in the process by adding additional precursor, thus increasing the capacity of the reactor for production of maleic anhydride. The amount of catalyst precursor fed to the regeneration zone depends on whether the objective is to maintain or increase the catalyst inventory. An amount of catalyst precursor in the range of 0.10 wt % to 15 wt % can be added at any time, the only restriction being that the rate of addition not be so great that the recirculating bed reactor temperature be decreased substantially below the desired operating temperature range. The added catalyst is calcined and reduced catalyst is oxidized in section 16 and the oxidized (regenerated) catalyst is then recycled to the fluidized bed section 10. The alternate/additional feed line 18 can be used to feed additional oxygen to the riser section 12. The recirculation solids reactor of this embodiment can also be operated with just the riser section 12 as the reaction zone. In this mode of operation the feed can be introduced into the riser section 12 through feed line 18.

Other types of recirculating solids reactors are useful in the practice of the invention, such as those described in U.S. Pat. No. 4,668,802, the teaching of which is incorporated by reference herein for such purpose. The reaction and regeneration zones can also be within a single reactor, although better process control usually is achieved if the two are in separate units.

The feed gas is comprised of a mixture of n-butane, air or oxygen (optional) and inert gas. The n-butane concentration in the feed gas can be from about 1 mole % to 100 mole %, preferably about 5 to about 20 mole %. Some of the n-butane used in the feed may be provided by the unconverted n-butane which is present in recycled reaction gas. In some instances, n-butane may be available as the predominant component in a mixture of gases including other hydrocarbons. As long as none of the other gases present significantly adversely affects the process, it may be more convenient to use this n-butane rich mixture in the feed gas as the source of n-butane. The oxygen concentration in the feed gas can be from 0 to about 20 mole %. Air can be used as the source of oxygen. The remainder of the feed, to 100 mole %, can be any inert gas, such as nitrogen or recycled reaction gas containing mostly carbon monoxide and carbon dioxide, and possibly unconverted n-butane. Oxidized V/P/O catalyst, along with any freshly calcined precursor that has just been added to the regenerator, is introduced into the reaction zone. The V/P/O particles are about 20 to about 300 μm in size. The butane oxidation is carried out at a temperature of about 300° C. to 500° C., preferably about 340° C. to about 450° C. The reactor exit gas pressure is typically 0–50 psig. The gas residence time in the reaction zone is about 0.5 second to about 15 seconds, and the catalyst residence time is about 2 seconds to about 5 minutes. The upper limit of catalyst residence time will, of course, depend on the activity of the catalyst. If still active the catalyst can be retained in the reaction zone for longer than 5 minutes.

The catalyst in the reactor effluent is separated from the effluent gases, and the maleic anhydride product is recovered from the effluent gases with both separations employing conventional techniques and equipment. The separated catalyst is referred to herein as the reduced catalyst because it is in a lower oxidation state than that of the fresh catalyst which enters the reaction zone. When appropriate to the embodiment, the reduced catalyst is preferably stripped of any reactor gases and then recycled to the regeneration zone. The stripped reactor gases are mixed with the reactor effluent gases. After maleic anhydride is recovered from the effluent gases of the reaction zone, the remaining gases may be vented or recycled to the reaction zone. Any off-gases or gas from the regeneration zone can be vented after heat recovery.

The regeneration zone temperature is maintained at about 300° C. to about 500° C., the catalyst residence time in the regeneration zone is about 5 seconds to, typically, about 5 minutes, and the oxygen-containing gas residence time is about 1 to about 30 seconds. Total gas flow rate and oxygen concentration must be sufficient to provide the needed oxygen for catalyst reoxidation to occur within the selected gas and catalyst residence time. The oxidized catalyst is then recycled to the reaction zone.

The required amount of catalyst and the required catalyst circulation rate depend on the extent to which the catalyst oxidation reaction is carried out in the regeneration zone (as opposed to the reaction zone), the amount of n-butane to be reacted, the amount of mobile (or reactive) oxygen contained by the catalyst, and the reaction zone process conditions that determine the amount of catalyst oxygen used per pass. When oxygen concentration in the reaction zone is low, or zero, and substantially all of the catalyst oxidation reaction is carried out in the regeneration zone, a high catalyst circulation rate is required. This rate may be reduced to the extent that some catalyst oxidation reaction is carried out in the reaction zone.

A circulating solids reactor can be operated continuously to oxidize n-butane without any gas phase oxygen in the reaction zone. Such operation results in higher selectivity to maleic anhydride than can be attained with conventional reactors, provided an adequate catalyst circulation rate is maintained to supply the needed oxidized catalyst. In order to minimize the gas phase oxygen in the reaction zone, gas phase oxygen is stripped from the oxidized catalyst before recycling the regenerated catalyst to the reaction zone.

Alternatively, if a recirculating solids reactor is operated to oxidize n-butane under conditions of temperature, oxygen and n-butane partial pressures, and residence time in the reaction zone similar to those used in conventional reactors, significantly higher conversion of n-butane and significantly higher yield of maleic anhydride are obtained.

The high selectivity to maleic anhydride attained in the recirculating solids reactor is maintained even if the feed to the reaction zone has a very high butane concentration. The feed can be 100% butane.

The V/P/O catalyst precursor compositions used in the process of the invention, which are attrition resistant or designed to be attrition resistant after calcination are made by procedures which are known to the art. The precursor compositions may incorporate catalyst promoters, components to improve attrition resistance or other beneficial components. The process of this invention is not limited to precursor compositions made by any particular method but the resulting catalyst must possess sufficient attrition resistance to withstand the rigors of a circulating bed reactor.

The catalyst precursors used in the examples of this invention were prepared by substantially following the procedures disclosed in U.S. Pat. No. 4,371,702, the teaching of which is incorporated by reference herein. The use of the expression "substantially following the procedures" is not intended as an implication that the same ingredients were employed but rather that the same general techniques were used.

The vanadium/phosphorus oxide (V/P/O) catalyst precursor can be made by a process wherein a conventional vanadium compound wherein the vanadium is in the +5 oxidation state, such as in $V_2O_5$ or $NH_4VO_3$, is partially reduced to the +4 oxidation state by reaction in either an aqueous or organic liquid medium. In an aqueous medium, the reductant can comprise a soluble inorganic compound, such as a halide acid, for example, concentrated hydrochloric acid; a reduced acid of phosphorus, for example, $H_3PO_3$; or a soluble organic compound, for example, formaldehyde, ethylene glycol, or glycolic, oxalic, citric or tartaric acid. In an organic medium, which is the preferred medium, the reductant can comprise an alcohol selected from such species as n-propyl, isopropyl, n-butyl, isobutyl, and benzyl alcohols. An organic medium is preferred since it gives higher surface area material from which a more active catalyst is subsequently obtained.

V/P/O catalyst precursor may also include a promoter which is a combination of selected materials, preferably introduced in both a specific order and chemical form, following the step in which the pentavalent vanadium compound is refluxed in an organic or aqueous medium. Suitable promoters comprise silicon and at least one of the variable valent elements selected from indium, antimony, and tantalum. In such a catalyst the Si/V atomic ratio is in the range 0.02–3.0:1.0, and the (In+Sb+Ta)/V atomic ratio is in the range 0.005–0.2:1.0, preferably 0.02–0.12:1.0. The P/V atomic ratio is in the range 0.9–1.3:1.0.

In an aqueous system for preparing the catalyst the silicon can be introduced in the form of a colloidal silica sol; for example, as one of the Ludox® colloidal silica compositions commercially available from E. I. du Pont de Nemours and Company. In the organic system, for example in an alcoholic medium, the silicon can be added as an alkyl orthosilicate; e.g., tetraethyl orthosilicate. When using an orthosilicate and $V_2O_5$ it is preferable to add at least 0.25 mole of orthosilicate per mole of $V_2O_5$ following refluxing the $V_2O_5$ in an organic or aqueous medium. The compositions which are useful in the process of the current invention have a Vox between 3.90 and 4.10.

Following reflux of the pentavalent vanadium compound in the organic or aqueous medium and optionally the introduction of the requisite promoter or promoter precursors the catalyst precursor is formed by the addition of any commonly used appropriate phosphorus compound; e.g., phosphoric acid in such amount that the P/V atomic ratio in the ultimate catalyst is in the range 0.9–1.3:1.0. The resultant mixture is heated under reflux to give the catalyst precursor composition that can be isolated by filtration, following cooling of the slurry to room temperature. This product is subsequently dried in air, inert gas or vacuum at 80° to 200° C. The drying atmosphere should be such that the tetravalent nature of the vanadium in the precursor is maintained.

It is highly preferred that for use in a fluidized bed or recirculating bed reactor the catalyst have good attrition resistance. This prolongs the catalyst life requiring less replacement catalyst or catalyst precursor to be added to the reactor and enables the maleic anhydride production process to be operated at peak efficiency for long periods of time thus improving overall performance from an economic standpoint. The preparation of catalyst precursor from which highly attrition resistant catalyst is produced is described in U.S. Pat. No. 4,677,084, the teaching of which is incorporated by reference herein for such purposes. V/P/O precursor particles made as described earlier are dispersed as a slurry in an aqueous silicic acid solution equivalent to a weight of $SiO_2$ not exceeding about 6 wt %. The relative amounts of the particles and silicic acid are chosen so that the weight of the $SiO_2$ formed is about 3–15% of the total weight of the particles and the $SiO_2$. The slurry is then spray dried to form porous microspheres of attrition resistant catalyst precursor having an average particle size of 10 to 300 microns, preferably 20 to 250 microns. This is calcined and activated by the process of the current invention. The catalyst precursor phase, $(VO)_2H_4P_2O_9$—3 to 15% $SiO_2$, must be converted to the catalytically active phase, $(VO)_2P_2O_7$—3 to 15% $SiO_2$ by calcination and activation. Besides accomplishing this structural transformation, these procedures must be carried out in such a way as to impart attrition resistance, combust residual organic matter contained in a precursor prepared in an organic medium and yield a highly active and selective catalyst.

Catalyst Evaluation:

The activated catalyst is evaluated for the production of maleic anhydride by the oxidation of n-butane in a recirculating solids reactor of the type illustrated in FIG. 1. The catalyst is charged to the reactor fluidized bed section and heated to about 380° C. while being fluidized in a gas stream having an average composition of 10% butane, 5.5% oxygen and 84.5% nitrogen. The average gas/solids contact time in the riser section reaction zone is about 1.5 seconds. The regeneration zone is also maintained at about 380° C. with an air stream and an average contact time of about 7.4 minutes. Steady state conditions are established and the average maleic anhydride production rate is determined by quenching the product stream with water and titrating the recovered maleic anhydride with 0.1N NaOH solution. The average maleic acid production rate is expressed as grams of maleic acid carbon generated per hour (grams C/hr.).

The following examples are presented to more fully demonstrate and further illustrate various individual aspects and features of the present invention. As such the examples are felt to be non-limiting and are meant to illustrate the invention but are not meant to be unduly limiting in any way particularly with respect to ultimate properties and advantages of the claimed improved process.

EXAMPLE 1

This example demonstrates that sufficient attrition resistance can be achieved during the relatively low temperature/short time exposure that catalyst precursor will experience after being added to the fluidized bed in a regenerator vessel.

Flash calcination experiments were conducted to simulate the fast heat-up time and short residence time experienced by catalyst precursor added directly to a regenerator vessel. Spray dried catalyst precursor $(VO)_2H_4P_2O_9$—10% $SiO_2$ was prepared by essentially the procedure of Example 1 of U.S. Pat. No. 4,677,084, omitting the addition of the catalyst promoter components $Si(OEt)_4$ and In metal. A thin bed of the spray dried catalyst precursor, contained in a gold foil boat, was introduced into a furnace pre-heated to the desired temperature. After inserting the sample and closing the furnace door, the set point temperature was typically re-established within 15 seconds. Upon reaching the desired duration of exposure, timed from the re-equilibration of the set point temperature, the sample was quenched by rapidly withdrawing it from the furnace and immediately placing it into a desiccator at ambient temperature.

A standardized attrition test, described in U.S. Pat. No. 4,677,084, was then performed on each sample. The principle of operation of this test, which allows comparison of the attrition resistance among different samples, is transfer of energy from a high velocity air jet from a precisely sized orifice to catalyst particles which in turn collide with other particles. Fines (particles with diameters less than about 16 microns) produced from these impacts are entrained in the upper gas flow and collected in a weighed flask fitted with a filter. The flask and filter are removed, dried and weighed at different elapsed times. The hourly rate of solid carry over between 6 and 24 hours is then calculated and represents the attrition rate. The orifice through which the air jet passes should be drilled to close tolerances because the attrition depends markedly on the diameter; i.e., on gas velocity. Some erosion of the hole occurs during use, and the plate must be replaced when the pressure drop through the plate deviates significantly from that obtained with a newly prepared plate under the same flow conditions. The apparatus described here and in U.S. Pat. No. 4,677,084 is substantially geometrically equivalent to that described by W. L. Forsythe, Jr. and W. R. Hertwig, Ind. and Eng. Chem. 41, 1200 (1949).

The following is a summary of flash calcination experiments conducted on spray dried catalyst precursor $(VO)_2H_4P_2O_9$—10% $SiO_2$. An attrition rate of less than about 0.10% is considered acceptable for use in the process of the invention.

| Attrition Rate | |
|---|---|
| Calcination Conditions | % weight loss/hour |
| no calcination | 0.18 |
| 390° C./1 hr/air (std.) | 0.08 |
| 390° C./1 hr/air (std.) | 0.04 |
| 370° C./2 min/air | 0.10 |
| 370° C./2 min/air | 0.04 |
| 370° C./1 min/air | 0.21 |
| 350° C./2 min/air | 0.09 |
| 350° C./1 min/air | 0.13 |

Based on these experiments it is concluded that sufficient attrition resistance can be imparted within a very brief calcination period. However, the residence time of spray dried catalyst precursor $(VO)_2H_4P_2O_9$—10%$SiO_2$ introduced into a regenerator vessel, where initial calcination in the presently disclosed process is conducted, should be greater than about 1 minute and most preferably greater than about 2 minutes. It should be recognized that this test is a worst case situation; in an operating recirculating solids reactor, the catalyst will not be subjected to the stress of thermal quenching, and instead will remain at elevated temperature and undergo additional calcination as it moves through the standpipe between vessels.

EXAMPLE 2

This example shows that maleic anhydride production in a recirculating solids reactor is maintained when a portion of the catalyst inventory is removed and an equivalent amount of catalyst precursor is added to the regenerator vessel. It also demonstrates that the attrition resistance of the catalyst remains high.

A spray dried, calcined/activated catalyst $(VO)_2P_2O_7$—10%$SiO_2$ was prepared by essentially the procedure of Example 1 of commonly assigned U.S. patent application Ser. No. (case CH-2309). This catalyst was evaluated for butane oxidation in a recirculating solids reactor system for the purpose of establishing a baseline catalytic performance. The conditions of this test were as follows: temperature of reaction, 380° C.; average feed composition to the riser reactor, 10% butane/5% oxygen/balance nitrogen; average gas/solids contact time in riser, 1.6 seconds; feed to fluidized bed regenerator, air; and average gas/solids contact time in regenerator, 5 minutes. After establishing baseline performance, about 15% of the catalyst inventory was removed while the reactor continued running at steady state. The catalyst inventory was then restored to its initial level by adding fresh spray dried catalyst precursor $(VO)_2H_4P_2O_9$—10%$SiO_2$, prepared as in Example 1 to the regenerator vessel. After 8 hours of steady state operation, a similar reduction of inventory and re-addition of fresh spray dried catalyst precursor was performed, bringing the total fraction of fresh, catalyst precursor added to about 27% of inventory.

Adding spray dried catalyst precursor to an operating transport bed reactor caused temporarily reduced performance that substantially recovered with time. The amount of maleic anhydride made decreased by 16% when the 27% substitution of catalyst precursor was first completed. After a further 30 hours of steady state operation at the standard operating conditions given above, the amount of maleic made recovered to within 3 to 5% of the initial baseline level. The calcination/activation process is known to occur at a significantly slower rate at the lower temperature of these operating conditions relative to the conventional calcination/activation process, (380° C. vs 460° C.). Thus, it is anticipated that complete activation (as judged by the maleic production achieving approximately 100% of the initial baseline level) would be achieved in a somewhat longer time period than the 30 hours over which this test was run.

Attrition resistance was also imparted to the catalyst while in the operating recirculating solids reactor as the following data, obtained on samples withdrawn from the reactor at the indicated times show:

| Attrition Rate | |
|---|---|
| Sample | % weight loss/hour |
| After initial baseline | 0.04 |
| 8 hrs after substitution of 15% of inventory by un-calcined and un-activated catalyst | 0.03 |
| 30 hrs after substitution of 27% of inventory by un-calcined and un-activated catalyst | 0.04 |

EXAMPLE 3

This example illustrates the beneficial effect, on the production rate of maleic anhydride, of increasing the V/P/O catalyst inventory during the operation of a recirculating bed reactor for the oxidation of n-butane.

Spray dried calcined/activated $(VO)_2P_2O_7$—10% $SiO_2$ catalyst was prepared by essentially the same process of Example 1 of commonly assigned U.S. patent application Ser. No. (case CH-2309). This catalyst was then evaluated for butane oxidation in a recirculating solids reactor system. The conditions of this test were as follows: 380° C.; average feed composition to the riser reactor, 10% butane/5.75% oxygen/balance nitrogen; average gas/solids contact time in the riser, 1.5 to 1.6 seconds; and feed to the fluidized bed regenerator, air. The useful inventory of catalyst was varied during the course of this test, while maintaining a nearly constant catalyst circulation rate. The change in catalyst inventory is indicated in the table below by the corresponding changes in regenerator bed height and gas/solids contact times in the regenerator.

| Regen. Bed Ht. cm. | Regen. Res. Time min. | Maleic Anhydride Product Rate grams C/hr |
| --- | --- | --- |
| 13.00 | 3.81 | 3.54 |
| 20.75 | 5.64 | 3.84 |
| 30.00 | 8.30 | 3.98 |
| 31.50 | 8.16 | 4.17 |
| 33.46 | 9.25 | 4.43 |

The data in the above table illustrate that increases in the production rate of maleic anhydride for a given catalyst circulation rate are achieved by increasing the catalyst inventory.

EXAMPLE 4

This example shows that catalyst precursor $(VO)_2H_4P_2O_9$—10% $SiO_2$ can be charged to a transport bed reactor and converted to active catalyst by circulating it through the reactor for an extended period of time while maintaining typical conditions for the oxidation of n-butane to maleic anhydride.

Spray dried catalyst precursor, $(VO)_2H_4P_2O_9$—10% $SiO_2$ prepared as in Example 1, was loaded to a recirculating solids reactor, preheated to 390° C. The charge was circulated for an extended period of time in the reactor under the following conditions: reactor temperature, 390° C.; average feed composition to the riser reactor, 10% butane/5% oxygen/balance nitrogen; average gas/solids contact time in riser, 1.6 seconds; feed to fluidized bed regenerator, air; and average gas/solids contact time in regenerator, 1.9 minutes. A sample of the charge was removed from the reactor after approximately 40 hours of circulation. The sample was subsequently evaluated for butane oxidation to maleic anhydride in a recirculating solids reactor for the purpose of establishing its catalytic performance. The conditions of this standardized, catalytic evaluation test were as follows: average temperature of reaction, 380° C.; average feed composition to the riser reactor, 10% butane/5.5% oxygen/balance nitrogen; average gas/solids contact time in riser, 1.6 sec; feed to fluidized bed regenerator, air; average gas/solids contact time in regenerator, about 8 min. The average maleic anhydride production rate given by the sample was 3.4 grams C/hr after 40 hours of circulation. This corresponds to a maleic anhydride production rate of about 83% of that obtained using an appropriate benchmark catalyst, such as spray dried calcined/activated catalyst, $(VO)_2P_2O_7$—10% $SiO_2$, prepared essentially by the procedure of Example 1 of commonly assigned U.S. patent application Ser. No. (case CH-2309).

Although the activation process is known to occur more slowly at the lower temperature conditions under which this catalyst was activated relative to a conventional activation process (390° C. vs. 460° C.), the catalyst activity after 40 hours recirculation under the conditions described above was sufficient to result in a very desirable maleic anhydride production rate.

Having thus described and exemplified the invention with a certain degree of particularity, it should be appreciated that the following claims are not to be so limited but are to be afforded a scope commensurate with the wording of each element of the claim and equivalents thereof.

We claim:

1. In a process for selective vapor phase oxidation of n-butane to maleic anhydride involving the use of a recirculating solids reactor comprising a reaction zone and a catalyst regeneration zone wherein n-butane is converted to maleic acid in the reaction zone of the recirculating solids reactor by use of a vanadium/phosphorous oxide catalyst in oxidized form and the reduced vanadium/phosphorous oxide catalyst is regenerated by contact with oxygen in the regeneration zone of the recirculating solids reactor; the specific improvement comprising: adding to the catalyst in the regeneration zone or to the recirculating solids sufficient vanadium/phosphorous oxide catalyst precursor or sufficient calcined vanadium/phosphorous oxide catalyst precursor to at least partially replenish catalysts losses associated with the catalyst recycling process at a rate of addition that effectuates in situ calcination and activation of the vanadium/phosphorous oxide catalyst precursor while maintaining the desired operating temperature of the n-butane to maleic anhydride conversion reaction and imparts attrition resistance in less than 5 minutes.

2. A process of claim 1 wherein vanadium/phosphorous oxide precursor is being added to the regeneration zone in the range of about 0.10 wt % to 15 wt % of the catalyst and the rate of addition not being so great that the recirculating bed reactor temperature be decreased below the desired operating temperature range of about 360° C. to about 500° C.

3. A process of claim 2 wherein said calcination of the vanadium/phosphorous oxide catalyst precursor and regeneration of the reduced vanadium/phosphorous oxide catalyst is performed using gas in the regeneration zone containing about 4 mole % to 25 mole % oxygen with the remainder up to 100 mole % being inert gas, at a catalyst residence time in the regeneration zone of up to 5 minutes and at an oxygen-containing gas residence time of up to about 30 seconds and a gas exit pressure of 0 psig to 50 psig.

4. A process of claim 3 wherein said calcination and regeneration is performed at a temperature of 360° C. to 450° C. using gas in the regeneration zone containing about 21 mole % oxygen.

5. A process according to claims 1, 2, 3, or 4 wherein said catalyst precursor or calcined catalyst precursor added is continually circulated between the reaction zone and catalyst regeneration zone achieving gradual activation under recirculating solids operating conditions.

* * * * *